(12) United States Patent
Kataoka et al.

(10) Patent No.: US 9,376,675 B2
(45) Date of Patent: *Jun. 28, 2016

(54) METHOD FOR PRESERVING COMPONENTS OF PANCREATIC JUICE IN A SAMPLE, AND KIT FOR PRESERVING COMPONENTS OF PANCREATIC JUICE IN A SAMPLE

(71) Applicant: OLYMPUS CORPORATION, Tokyo (JP)

(72) Inventors: Rie Kataoka, Tokyo (JP); Nao Moriya, Tokyo (JP); Hiromi Sanuki, Yokohama (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/576,437

(22) Filed: Dec. 19, 2014

(65) Prior Publication Data

US 2015/0104846 A1 Apr. 16, 2015

Related U.S. Application Data

(63) Continuation of application No. PCT/JP2013/055828, filed on Mar. 4, 2013.

(30) Foreign Application Priority Data

Jun. 22, 2012 (JP) ................... 2012-140796

(51) Int. Cl.
*C12N 9/99* (2006.01)
*C09K 15/28* (2006.01)
*G01N 33/574* (2006.01)

(52) U.S. Cl.
CPC . *C12N 9/99* (2013.01); *C09K 15/28* (2013.01); *G01N 33/57438* (2013.01)

(58) Field of Classification Search
None
See application file for complete search history.

(56) References Cited

U.S. PATENT DOCUMENTS

2009/0215182 A1 8/2009 Schellenberger et al.

FOREIGN PATENT DOCUMENTS

| CN | 101547702 A | 9/2009 |
|---|---|---|
| CN | 103781904 A | 5/2014 |
| EP | 2 696 202 A1 | 2/2014 |
| EP | 2 757 151 A1 | 7/2014 |
| JP | 2005-525126 A | 8/2005 |
| JP | 2007-222062 A | 9/2007 |
| JP | 2010-025770 A | 2/2010 |
| JP | 496407 | 7/2010 |
| JP | 2011-5009 A | 1/2011 |
| JP | 2011-047802 A | 3/2011 |
| WO | WO 03/097237 A2 | 11/2003 |
| WO | WO 2012/137832 A1 | 10/2012 |
| WO | WO 2013/038981 A1 | 3/2013 |

OTHER PUBLICATIONS

The Complete Guide for Protease Inhibition, Roche Molecular Biochemicals, 2001, Retrieved from: < http://wolfson.huji.ac.il/purification/PDF/Protease_Inhibitors/ProteaseInhibitorRoche.pdf > on Sep. 8, 2015.*
Paulo et al., "Optimized sample preparation of endoscopic collected pancreatic fluid for SDS-PAGE analysis", Electrophoresis 2010, 31, 2377-2387.*
Product Information for cOmplete, Mini (Cat. No. 11836153001); Roche, 2005. Retrieved from < http://labs.mmg.pitt.edu/gjoerup/protease%20inhibitor.pdf > on Sep. 8, 2015.*
Ohuchida et al., "S100P Is an Early DevelopmentalMarker of Pancreatic Carcinogenesis", Clin Cancer Res 2006;12(18):5411-5416.*
International Search Report dated Apr. 16, 2013 issued in PCT/JP2013/055828.
Furui T. et al., "Protein Degradation in Human Pure Pancreatic Juice Analyzed by Two-Dimensional Gel Electrophoresis", Electrophoresis 17:797-802 (Jan. 1, 1996).
Sarfati P. et al., "Evidence of a New Serine Protease in the Rat Pure Pancreatic Juice that Degrades Somatostatin", Life Sciences 47(12):1043-1049 (Jan. 1, 1990).
Steiner J.M. et al., "Purification of Classical Pancreatic Lipase from Dog Pancreas", Biochimie 84(12)1243-1251 Dec. 1, 2002).
"The Complete Guide for Protease Inhibition", (20 pages) (Aug. 1, 2007).
"Protease Inhibitor Panel Product Information", (9 pages) (Sep. 8, 2005).
Extended European Search Report dated Nov. 5, 2015 received in European Patent Application No. 13 80 6851.5.
Ehara K., "Suiekichu Ni Okeru Lipase Kassei No Shikkatsu No Yoin Ni Tsuite No Kenkyu", The Journal of Medical Technology, Eisei Kensa 31(7):1039-1042 (1982).
Hausmann D.H.F. et al., "Cu/Zn-SOD in Human Pancreatic Tissue and Pancreatic Juice", International Journal of Pancreatology 22(3):207-213 (Dec. 1997).

(Continued)

*Primary Examiner* — Suzanne M Noakes
(74) *Attorney, Agent, or Firm* — Scully, Scott, Murphy & Presser, P.C.

(57) ABSTRACT

The present invention provides a method for preserving biological components in pancreatic juice, and a kit suited for this method. The method involves adding, to a pancreatic juice-containing biological sample, at least one sulfonyl fluoride-containing protease inhibitor and at least one trypsin-like serine protease inhibitor belonging to a group of amino acid chloromethyl ketones.

8 Claims, 4 Drawing Sheets

(56) References Cited

OTHER PUBLICATIONS

Holm H. et al., "Raw Soy and Purified Proteinase Inhibitors Induce the Appearance of Inhibitor-Resistant Trypsin and Chymotrypsin Activities in Wistar Rat Duodenal Juice", Journal of Nitrition 121:532-538 (1991).

Kaino S. et al., "Two-Dimensional Zymography for Analysis of Proteolytic Enzymes in Human Pure Pancreatic Juice", Electrophoresis 19(5):782-787 (1998).

Katsunuma T. et al., Analysis, vol. 10:682-689 (1978), together with a partial English-language translation.

Kukor Z. et al., "Presence of Cathepsin B in the Human Pancreatic Secretory Pathway and its Role in Trypsinogen Activation During Hereditary Pancreatitis", The Journal of Biological Chemistry 277(24):21389-21396 (Jun. 14, 2002).

Ulleberg E.K. et al., "Human Gastrointestinal Juices Induced for Use in In Vitro Digestion Models", Food Digestion 2:52-61 (Oct. 15, 2011).

Wandschneider S. et al., "Autoimmune Pancreatic Disease: Preparation of Pancreatic Juice for Proteome Analysis", Electrophoresis 22(20):4383-4390 (2001).

Yokoyama M. et al., "Matrix Metalloproteinase-2 in Pancreatic Juice for Diagnosis of Pancreatic Cancer", Pancreas 24(4):344-347 (2002).

Chinese Office Action dated Feb. 9, 2015 received from Chinese Application No. 201280043967.7, together with an English-language translation.

Chinese Office Action dated Sep. 17, 2015 received from Chinese Application No. 201380032761.9, together with an English-language translation.

Extended Supplementary European Search Report dated Jan. 29, 2015 from European Application No. 12 83 1055.4.

International Search Report dated Aug. 28, 2012 received from International Application No. PCT/JP2012/066004.

U.S. Final Office Action dated Aug. 19, 2015 received in U.S. Appl. No. 14/200,188.

U.S. Office Action dated May 11, 2015 received in U.S. Appl. No. 14/200,188.

\* cited by examiner

METHOD FOR PRESERVING COMPONENTS OF PANCREATIC JUICE IN A SAMPLE, AND KIT FOR PRESERVING COMPONENTS OF PANCREATIC JUICE IN A SAMPLE

CROSS-REFERENCE TO RELATED APPLICATIONS

The present application is a U.S. continuation application based on PCT International Patent Application PCT/JP2013/055828, filed on Mar. 4, 2013, the contents of which are incorporated herein by reference.

FIELD OF THE INVENTION

The present invention relates to a method for preserving and storing biological components of pancreatic juice.

BACKGROUND

Pancreatic juice is a fluid secreted from the exocrine portion of the pancreas into the duodenum of the small intestine. It has been used to detect gastrointestinal infection, bicarbonate levels, and to search for possible biomarkers for pancreatic cancer, as currently pancreatic cancer is not found in early stages and, when detected in advanced stages, has a poor prognosis.

S100P (S100 calcium binding protein P) is a member of the S100 family of proteins containing 2 EF-hand calcium-binding motifs. S100 proteins are implicated in the regulation of cellular processes such as cell cycle progression and differentiation. S100P is a receptor for advanced glycation end products (RAGE) in pancreatic cancer and is associated with growth and invasion of pancreatic cancer. For example, it has been reported in Ohuchida et al., Clinical Cancer Research, 2006, Vol. 12, No. 18, pp. 5411-5416, that S100P represents a potential early marker of pancreatic cancer, and analysis of S100P concentration in pancreatic juice is useful for discriminating between tumor and chronic pancreatitis. It has further been reported in Nakata et al., Human Pathology, 2010, Vol. 41, pp. 824-831, that expression of S100P is not observed in normal pancreatic ductal epithelium, but is observed in intraductal papillary mucinous tumor cells. This suggests that S100P could represent a marker for pancreatic cancer, and measurement of S100P in pancreatic juice is expected to be useful for early detection, diagnosis, and/or staging of pancreatic cancer.

Pancreatic juice contains various digestive enzymes that are present in inactive form in the pancreas, but are activated after excretion into the duodenum. A cascade degradation reaction of digestive enzymes in pancreatic juice is initiated by enterokinase secreted from duodenal epithelial cells. Specifically, trypsinogen in pancreatic juice is converted into its active trypsin form by enterokinase, which then activates digestive enzymes/proteases such as chymotrypsinogen and proesterase. In the presence of these activeproteases, biological molecules such as proteins, nucleic acids, lipids, and cells contained in pancreatic juice are degraded or modified after excretion into the duodenum. Therefore, it may be difficult to determine the levels of biological molecules in a sample of pancreatic juice excreted into the duodenum, due to the influence of proteases and digestive enzymes in the biological sample.

SUMMARY OF THE INVENTION

Disclosed herein are methods to inhibit the activity of proteases in pancreatic juice. It has been found that by adding a specific combination of sulfonyl fluoride-containing protease inhibitors and a trypsin-like serine protease inhibitors to biological sample containing pancreatic juice, biological molecules such as proteins and proteinaceous components contained in the biological sample can be stored stably, whether stored frozen or at room temperature.

Accordingly, disclosed herein are methods for preserving a proteinaceous component of pancreatic juice in a sample and kits for preserving proteinaceous components of pancreatic juice in a sample, as follows:

(1) A method for preserving a proteinaceous component of pancreatic juice in a sample, including a step of adding, to a biological sample with pancreatic juice components, at least one sulfonyl fluoride-containing protease inhibitor and at least one trypsin-like serine protease inhibitor belonging to a group of amino acid chloromethyl ketones, in an amount sufficient to preserve a proteinaceous component of the pancreatic juice.

(2) The method as described above in (1), further including a step of storing the sample at room temperature.

(3) The method as described above in (1), wherein the sulfonyl fluoride-containing protease inhibitor is selected from the group consisting of phenylmethylsulfonyl fluoride (PMSF), 4-(2-aminoethyl)-benzenesulfonyl fluoride) (AEBSF), p-APMSF, 4-(fluorosulfonyl)benzoic acid, 3-(fluorosulfonyl)benzoic acid, 2-aminobenzenesulfonyl fluoride, 3-aminobenzenesulfonyl fluoride, 4-aminobenzenesulfonyl fluoride, 2-nitrobenzenesulfonyl fluoride, 3-nitrobenzenesulfonyl fluoride, and 4-nitrobenzenesulfonyl fluoride.

(4) The method as described above in (1) or (2), wherein as the sulfonyl fluoride-containing protease inhibitor, two or more compounds selected from the group consisting of PMSF, AEBSF, and p-APMSF are used.

(5) The method as described above in any of (1) to (3), wherein the trypsin-like serine protease inhibitor is N-a-tosyl-L-lysine chloromethyl ketone (TLCK).

(6) The method as described above in (1), wherein in the step of preserving the proteinaceous component of pancreatic juice in a sample, PMSF, AEBSF, or p-APMSF is added as the sulfonyl fluoride-containing protease inhibitor to give a final concentration of at least 1 mMPMSF, at least 4 mM AEBSF, and at least 2 mM p-APMSF, and TLCK is added to a final concentration of at least 0.1 mM.

(7) The method as described above in any one of (1) to (5), wherein the biological sample is a pancreatic juice or a duodenal juice.

(8) The method as described above in (1), wherein the proteinaceous component is S100 calcium binding protein P (S100P).

(9) Further disclosed is a kit for preserving proteinaceous components of pancreatic juice in a sample, having at least one sulfonyl fluoride-containing protease inhibitor and at least one trypsin-like serine protease inhibitor belonging to a group of amino acid chloromethyl ketones.

(10) The kit as described above in (9), wherein the sulfonyl fluoride-containing protease inhibitor is at least one compound selected from the group consisting of phenylmethylsulfonyl fluoride (PMSF), 4-(2-aminoethyl)-benzenesulfonyl fluoride) (AEBSF), and p-APMSF.

(11) The kit as described above in (9) or (10), wherein the trypsin-like serine protease inhibitor is N-a-tosyl-L-lysine chloromethyl ketone (TLCK).

(12) The kit as described above in any one of (9) to (11), further having a storage container equipped with a reservoir portion for retaining therein a collected body fluid, the reservoir portion being filled in advance with the sulfonyl fluoride-containing protease inhibitor and the trypsin-like serine protease inhibitor.

DETAILED DESCRIPTION

Figure 1:
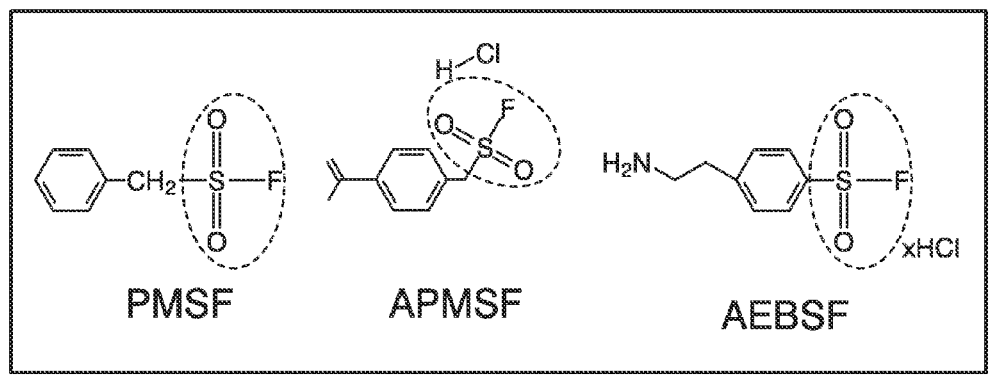
FIG. 1 shows chemical formulas of PMSF, AEBSF, and p-APMSF, respectively.

Pancreatic juice is a body fluid excreted from the pancreatic duct. A "sample containing pancreatic juice", as used in the present invention and present specification, means a sample containing a body fluid containing a pancreatic juice derived component. Examples of samples containing pancreatic juice include pancreatic juice collected from the pancreas directly through a catheter, and fluid collected in the duodenum (duodenal juice). The duodenal juice contains, in addition to the pancreatic juice, bile excreted from the papillary portion and a fluid, blood, and the like originally present in the duodenum. The pancreatic juice or duodenal juice can be collected in a manner known per se in the art.

<Method for Preserving a Proteinaceous Component of Pancreatic Juice in a Sample>

The method for preserving a proteinaceous component of pancreatic juice in a sample as disclosed herein (which may hereinafter be called "preservation method") is a method for preserving a proteinaceous component of pancreatic juice in a sample to permit stable storage of the sample while inhibiting degradation or modification of proteinaceous components, such as S100 calcium binding protein P (S100P), contained in the biological sample. Described specifically, the preservation method disclosed herein is characterized in that it has a step of adding, to a pancreatic juice-containing biological sample, at least one sulfonyl fluoride-containing protease inhibitor and at least one trypsin-like serine protease inhibitor belonging to a group of amino acid chloromethyl ketones to prepare a pancreatic juice-containing sample and in addition, it has an optional step of storing the sample at room temperature until the sample is subjected to detection of S100P.

Pancreatic juice contains a large amount of proteases as well as proteins to be tested (for example, S100P), so that when a biological sample with pancreatic juice is stored, the proteinaceous components are degraded or modified due to the proteolytic activity of the proteases. When such a biological sample is tested after storage, target proteins will typically be detected at reduced levels, or not be detected at all, thus providing inaccurate test results. When a pancreatic juice-containing biological sample is prepared by using the preservation methods of disclosed herein, however, the activity of the proteases derived from the biological sample can be effectively suppressed and stability of proteinacious components can be improved drastically. The pancreatic juice-containing sample obtained using the preservation method disclosed herein has a quality higher than ever even after storage at room temperature and it is therefore suited for testing proteins (such as detecting S100P) in biological samples with pancreatic juice.

More specifically, in the preservation disclosed herein, the pancreatic juice-containing sample is prepared by adding at least one sulfonyl fluoride-containing protease inhibitor and at least one trypsin-like serine protease inhibitor belonging to a group of amino acid chloromethyl ketones (which may hereinafter be called "specific trypsin-like serine protease inhibitor"). By using the sulfonyl fluoride-containing protease inhibitor and the trypsin-like serine protease inhibitor in combination, degradation or modification of proteinaceous components, such as S100P, by pancreatic proteases, can effectively be suppressed, even during storage at room temperature.

As described in Example 1, amino acid chloromethyl ketones such as TLCK (N-a-tosyl-L-lysine chloromethyl ketone) are not effective inhibitors by themselves in suppressing the activity of proteases in pancreatic or duodenal juice that of relative to known inhibitors such as Foipan, FOY, or leupeptin. However, the combination of a sulfonyl fluoride-containing protease inhibitor and a trypsin-like serine protease inhibitor belonging to a group of amino acid chloromethyl ketones such as TLCK has an excellent effect of improving the stability of S100P relative to the combination of a sulfonyl fluoride-containing protease inhibitor and another protease inhibitor, such as leupeptin. This unexpected finding, that combined use of a sulfonyl fluoride-containing protease inhibitor and a trypsin-like serine protease inhibitor belonging to a group of amino acid chloromethyl ketones is particularly effective for improving the stability of proteinaceous components in pancreatic juice, was identified for the first time by the present inventors.

The type of sulfonyl fluoride-containing protease inhibitor to be used in the preservation methods disclosed herein is not particularly limited as long as it is a compound having a sulfonyl fluoride group and at the same time, having protease inhibitory activity. However, compounds having a structure in which a sulfonyl fluoride group is bound to a benzene ring directly or through a hydrocarbon group having from 1 to 6 carbon atoms may be used, of which PMSF (phenylmethylsulfonyl fluoride), AEBSF (4-(2-aminoethyl)-benzenesulfonyl fluoride)), p-APMSF (p-amidinophenylmethanesulfonyl fluoride hydrochloride), 4-(fluorosulfonyl)benzoic acid (CAS No. 455-26-5), 3-(fluorosulfonyl)benzoic acid (CAS No. 454-95-5), 2-aminobenzenesulfonyl fluoride (CAS No. 392-86-9), 3-aminobenzenesulfonyl fluoride (CAS No. 368-50-3), 4-aminobenzenesulfonyl fluoride (CAS No. 98-62-4), 2-nitrobenzenesulfonyl fluoride (CAS No. 433-98-7), 3-nitrobenzenesulfonyl fluoride (CAS No. 349-78-0), or 4-nitrobenzenesulfonyl fluoride (CAS No. 349-96-2) may be used. The chemical formulas of PMSF, AEBSF, and p-APMSF are shown in FIG. 1, respectively. The functional group surrounded with a dotted line in FIG. 1 is a sulfonyl group.

The sulfonyl fluoride-containing protease inhibitors to be used in the preservation method disclosed herein may be used either singly or in combination of two or more. In one embodiment, at least one compound selected from the group consisting of PMSF, AEBSF, and p-APMSF is used. and In another embodiment, two or more compounds selected from the group consisting of PMSF, AEBSF, and p-APMSF is used. In a further embodiment, all three compounds are used.

The amount of the sulfonyl fluoride-containing protease inhibitor to be added to the pancreatic juice-containing biological sample is an amount at which the protease inhibitor can produce a protease inhibiting effect and an effect of improving the stability of proteinaceous components, such as S100P, in the sample. It can be adjusted as needed in consideration of the kind of proteinacious component to be targeted, the type of pancreatic juice-containing biological sample, and the protease inhibitor or inhibitors to be used. For example, when only PMSF is added as the sulfonyl fluoride-containing protease inhibitor to the sample, it can be added to give a final concentration of 1 mM or more, 5 mM or more, or 10 mM or more. In another example, when only AEBSF is used as the sulfonyl fluoride-containing protease inhibitor, AEBSF can be added to the sample to give a final concentration of 4 mM or more, 10 mM or more, or 20 mM or more. In a further example, when only p-APMSF is added as the sulfonyl fluoride-containing protease inhibitor, p-APMSF can be added to the sample to give a final concentration of 2 mM or more, 5 mM or more, or 10 mM or more.

The trypsin-like serine protease inhibitor to be used in the preservation method disclosed herein can be any compound that belongs to a group of amino acid chloromethyl ketones and has inhibitory activity against trypsin-like serine proteases typified by trypsin. In one embodiment, TLCK is used as the amino acid chloromethyl ketone.

The specific trypsin-like serine protease inhibitor to be added to the pancreatic juice—is added in an amount at which this protease inhibitor can produce a protease inhibitory effect and an effect of improving stability of proteinaceous components in the sample. It can be adjusted as needed in consideration of the kind of the pancreatic juice-containing biological sample, the kind of the protease inhibitor to be used, and the like. For example, where only TLCK is added as the specific trypsin-like serine protease inhibitor to the pancreatic juice-containing biological sample, it can be added to give a final concentration of 0.1 mM or more, 1 mM or more, 5 mM or more, or 10 mM or more.

In the preservation method disclosed herein, each of the sulfonyl fluoride-containing protease inhibitor and the specific trypsin-like serine protease inhibitor to be added to the pancreatic juice component-containing biological sample may be either in solid form such as powders or granules or in the form of a protease inhibitor solution obtained by dissolving it in a proper buffer or the like. The sulfonyl fluoride-containing protease inhibitor and the specific trypsin-like serine protease inhibitor may be added to the pancreatic juice-containing biological sample simultaneously or after addition of one of them, the other one may be added. From the standpoint of sufficiently producing the effect disclosed herein for improving the room stability of proteins in a sample, simultaneous addition of the sulfonyl fluoride-containing protease inhibitor and the specific trypsin-like serine protease inhibitor may be used.

In some embodiments of the disclosed method, other protease inhibitors may be used in addition to a sulfonyl fluoride-containing protease inhibitor and a specific trypsin-like serine protease inhibitor. Examples of other protease inhibitors include peptide-based protease inhibitors such as aprotinin, leupeptin, antipain, chymostatin, elastatinal, and antithrombin, chelating agents such as EDTA, elastase inhibitors, trypsin inhibitors, and Ecotin (E. coli). In addition, drugs for pancreatitis such as gabexate mesilate (FOY), camostat mesilate (Foipan), nafamostat mesilate (Futhan), and urinastatin can also be used.

The pancreatic juice-containing biological sample may be any biological sample containing a pancreatic juice-derived proteinaceous component. It may be any of a sample composed only of a body fluid containing a pancreatic juice-derived component, a liquid obtained by diluting the body liquid with a proper buffer or the like, or a mixture obtained by adding, to the body liquid or diluted liquid, various additives such as surfactants, nucleolytic enzyme inhibitors, pH regulators, and pH indicators. In a specific embodiment, the sample is a sample containing pancreatic juice, duodenal juice, diluted pancreatic juice, diluted duodenal juice, and mixtures obtained by adding thereto the above-mentioned various additives.

In the preservation method disclosed herein, the sulfonyl fluoride-containing protease inhibitor, and the trypsin-like serine protease inhibitor belonging to a group of amino acid chloromethyl ketones, is added to the pancreatic juice-containing biological sample after collection from a living body. The time interval between collection of the biological sample and addition thereto of these protease inhibitors is preferably as short as possible, and preferably immediately after collection from a living body. In the pancreatic juice-containing biological sample, proteases have very strong action and proteolysis proceeds immediately after collection, so it may be optimal (although not required) to immediately add the protease inhibitors to the sample.

For example, a reservoir portion (a container-like member for retaining a collected body fluid therein) of a collection tool for collecting pancreatic juice or duodenal juice from a living body can be pre-filled with a sulfonyl fluoride-containing protease inhibitor and a trypsin-like serine protease inhibitor belonging to a group of amino acid chloromethyl ketones. Thus, pancreatic juice or duodenal juice collected from the living body can be mixed with the protease inhibitors in a collection container during collection of the sample. When the collection tool is not equipped with a reservoir portion, and a storage container serving as a reservoir portion is connected to the collection tool, the storage container may be itself pre-filled with the sulfonyl fluoride-containing protease inhibitor and the trypsin-like serine protease inhibitor belonging to a group of amino acid chloromethyl ketones.

In the preservation process disclosed herein, pancreatic juice-derived proteinaceous components can be stored more stably than ever before, even at room temperature. It is therefore possible to test the level or function of proteins such as S100P in a sample containing pancreatic juice which is preserved by the disclosed methods, with sufficient test accuracy even when the sample is stored at room temperature until it is tested for protein levels or protein function. Samples preserved by the disclosed methods can be stored at room temperature, or stored in frozen or refrigerated form.

Expression of proteins, such as S100P, in a pancreatic juice-containing sample prepared by the preservation method disclosed herein can be detected by various protein analyses using ELISA, immunochromatography, two-dimensional electrophoresis, western blotting, or mass analysis, various nucleic acid analyses using PCR, RT-PCR, or hybridization with a probe, and cell analyses such as counting of the cell number or cytology.

The preservation method disclosed herein can also preserve pancreatic juice-derived components other than S100P. The pancreatic juice-containing sample prepared by the preservation method disclosed herein can therefore be used also as a measurement sample for various tests of a component, other than S100P, in the sample. A substance to be tested is not particularly limited as long as it is a biological component expected to be contained in pancreatic or duodenal juice. It may be a protein, it may be a nucleic acid such as DNA or RNA, or it may be a cell. For example, the pancreatic juice-containing sample can be used for various protein analyses using ELISA, immunochromatography, two-dimensional electrophoresis, western blotting, or mass analysis, various nucleic acid analyses using PCR, RT-PCR, or hybridization with a probe, and cell analyses such as counting of the cell number and cytology.

<Kit for Storing a Pancreatic Juice-Containing Biological Sample>

The kit for storing a pancreatic juice-containing biological sample as disclosed herein is characterized in that it has at least one sulfonyl fluoride-containing protease inhibitor and at least one trypsin-like serine protease inhibitor belonging to a group of amino acid chloromethyl ketones. By adding a sulfonyl fluoride-containing protease inhibitor and a specific trypsin-like serine protease inhibitor which the storage kit has to a pancreatic juice-containing biological sample, a pancreatic juice-containing sample which can be stored at room temperature until it is provided for the detection of S100P can be prepared more simply and easily.

The sulfonyl fluoride-containing protease inhibitors to be included in the storage kit disclosed herein may be either singly or used in combination of two or more. In the present invention, using at least one compound selected from the group consisting of PMSF, AEBSF, and p-APMSF may be used, with using two or more compounds selected from this compound group being used. Similarly, the trypsin-like serine protease inhibitors to be included in the storage kit disclosed herein may be used either singly or in combination of two or more. In an aspect disclosed herein, using TLCK as the trypsin-like serine protease inhibitor may be used.

The various protease inhibitors included in the storage kit disclosed herein may be in the form of lyophilized powders or in the form of tablets, granules, or the like formed from the lyophilized powders together with a proper excipient and the like. They may be provided in the form of a solution of a protease inhibitor dissolved in a proper buffer.

The storage kit disclosed herein may further contain a buffer for diluting a collected body fluid, another protease inhibitor, a surfactant, a pH regulator, a pH indicator, or the like. Various additives such as surfactant, pH regulator, and pH indicator may be dissolved in a diluting buffer in advance. Further, the storage kit disclosed herein may include, in order to permit dropwise addition of a predetermined amount of a prepared pancreatic juice-containing sample (obtained by adding, to a pancreatic juice-containing biological sample, various protease inhibitors included in the storage kit disclosed herein and then adding, if necessary, another component) from a container filled with the pancreatic juice-containing sample, a cap that can be attached to an opening portion of the container.

The storage kit disclosed herein may include a storage container equipped with a reservoir portion for retaining therein a body fluid, such as pancreatic juice or duodenal juice, collected from a living body. In this case, the protease inhibitors disclosed herein may be contained in the reservoir portion in advance. When the storage container has been graduated, the amount of the biological sample charged in the storage container (a total amount of the biological sample and the protease inhibitors when the storage container is filled with the protease inhibitors in advance) can be confirmed visually and further, a final concentration of the protease inhibitors can be found at a glance.

It is the common practice to collect the pancreatic juice-containing biological sample transendoscopically. As a constituent of the storage kit disclosed herein, the kit may include a collecting tool for transendoscopically collecting the pancreatic juice-containing biological sample. Examples of the collecting tool include a combination of a catheter that can be inserted into an endoscopic device and a syringe and a probe equipped, at the end thereof, with an absorber that can be inserted into an endoscopic device. Examples of the catheter that can be inserted into an endoscopic device include a specimen collecting cube described in Japanese Patent No. 2011-5009. These collecting tools may have a reservoir portion in which the protease inhibitors have been dispensed in advance. When the reservoir portion is removable, it can also be used as a storage container.

EXAMPLES

An aspect of the present invention will hereinafter be described in further detail by Examples and the like but the present invention is not limited to or by the following Examples.

Example 1

A protease inhibitor screen was performed to find an inhibitor targeting a serine protease and having a high inhibitory effect against pancreatic juice. The protease inhibitors used were aprotinin (product of Roche), leupeptin (product of Roche), PMSF (product of Roche), AEBSF (product of Roche), p-APMSF (product of SIGMA), camostat mesilate (Foipan: product of Wako Pure Chemical Industries), gabexate mesilate (FOY: product of Wako Pure Chemical Industries), TLCK (product of SIGMA), and TPCK (product of SIGMA). It is to be noted that TPCK is an amino acid chloromethyl ketone having inhibitory activity against chymotrypsin but having no inhibitory activity against trypsin.

"Pancreatin", a digestive enzyme prepared from the pig pancreas in which a pancreatic enzyme was present in activated form was used as pseudo artificial pancreatic juice. After addition of protease inhibitors in an amount so that the final concentration thereof would fall within a concentration range recommended by the manufacturers of the inhibitors, the protease activity was measured. The protease activity was measured using EnzCheck Protease Assay Kits (product of Molecular Probes). Described specifically, fluorescently-labeled casein attached to a kit was added to a pancreatin solution containing each protease inhibitor. After incubation at 37° C. for 2 hours, the amount of fluorescence was measured at a fluorescence wavelength of Ex/Em=485/535 nm. As a control, the protease activity of a sample solution (containing no inhibitor) obtained by directly adding fluorescently-labeled casein to pancreatin was measured.

Figure 2:
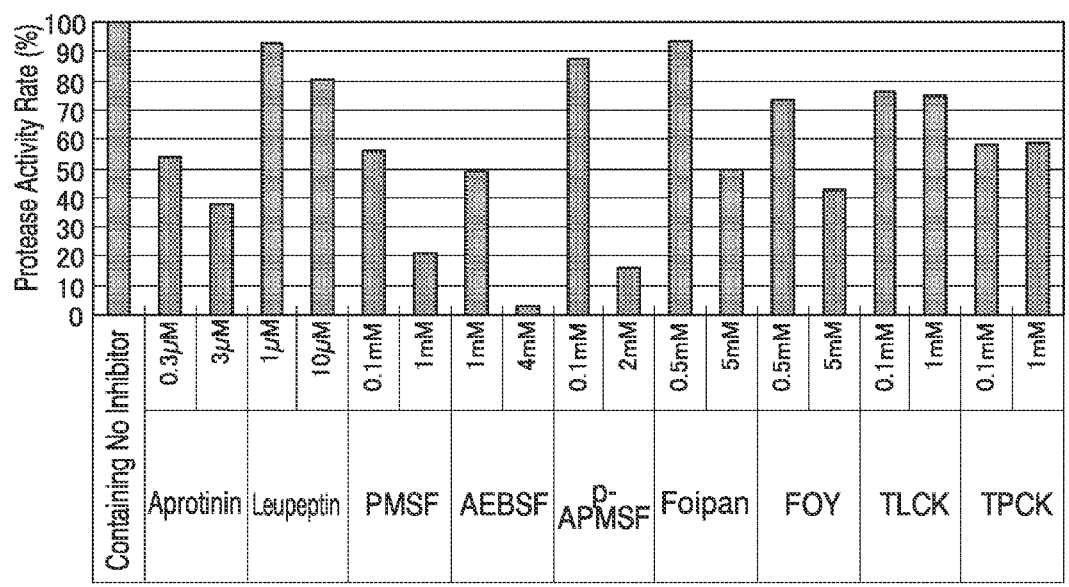
FIG. 2 shows the results of the protease activity (relative value: %) of respective pancreatin solutions in Example 1.

Measurement results of the amount of fluorescence of each of the pancreatin solutions are shown in FIG. 2. The amount of fluorescence plotted along the ordinate represents the amount of degraded casein and it was approximated as the value of protease activity. The protease inhibitors contained respectively in the pancreatin solutions and final concentrations thereof are plotted along the abscissa. The results have suggested that PMSF, AEBSF, and p-APMSF have a markedly high inhibitory effect compared with the other protease inhibitors. These inhibitors are each a sulfonyl fluoride-containing sulfone-based compound.

Example 2

While attention was paid to the sulfone-based compounds found to have a high inhibitory effect against digestive enzymes in pancreatic juice in Example 1, the effect of the various sulfone-based compounds on the room temperature stability of S100P (calcium-binding protein) known as a marker protein of pancreatic cancer was studied. This means that by using four human clinical pancreatic juice specimens, whether the concentration of S100P changed or not after addition of a S100P protein standard preparation was studied before and after room temperature storage.

Described specifically, sample solutions were prepared as follows: (1) Sample Solution 1: containing no inhibitor, obtained by mixing 25 ng/mL of an S100P (standard preparation) solution with the human clinical specimens, respectively. (2) Sample Solution 2: AEBSF, obtained by adding AEBSF (final concentration: 4 mM) to Sample Solution 1. (3) Sample Solution 3: AEBSF+PMSF, obtained by adding both AEBSF (final concentration: 4 mM) and PMSF (final concentration: 1 mM) to Sample Solution 1. The sample solutions were each prepared using a buffer attached to CircuLex S100P ELISA Kit (product of Cyclex, Catalogue Number: CY-8060). The sample solutions thus obtained were each allowed to react by incubating at 25° C. for 16 hours (room temperature storage). Then, S100P was detected using CircuLex S100P ELISA Kit (product of Cyclex, Catalogue Number: CY-8060) from solutions obtained by carrying out 10-fold dilution of the sample solutions with a buffer attached to CircuLex S100P ELISA Kit, respectively. As a control, S100P was detected similarly from Sample Solution 1 immediately after preservation (that is, before room temperature storage).

Figure 3:
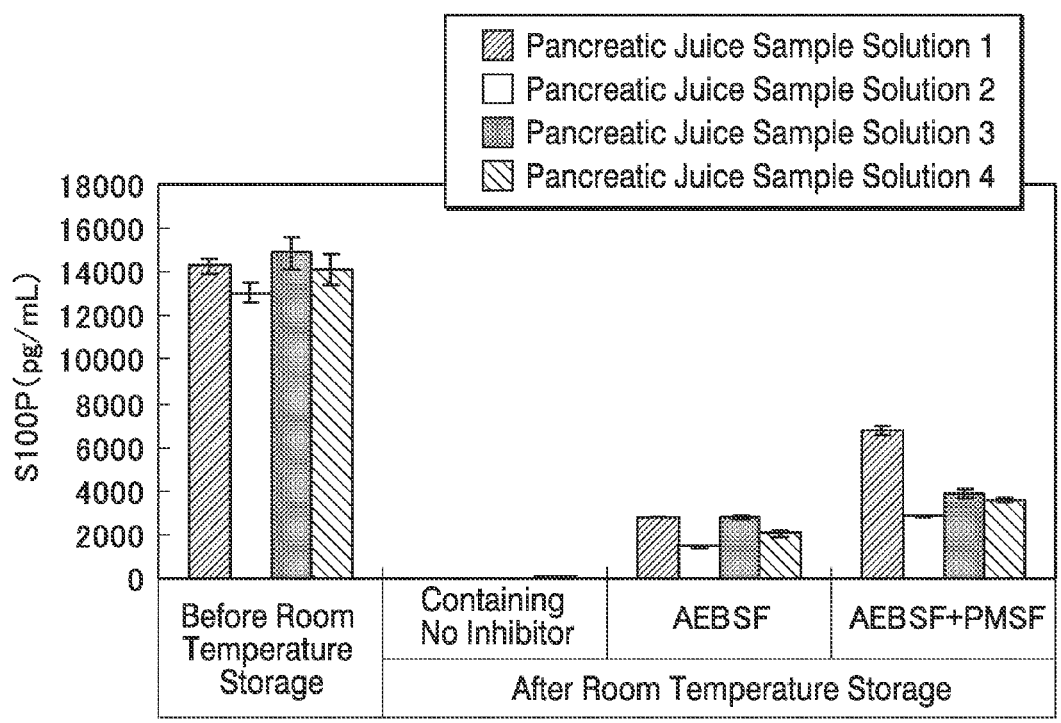
FIG. 3 shows the measurement results of the amount of S100P in the respective sample solutions in Example 2.

The measurement results are shown in FIG. 3. The S100P concentration is plotted along the ordinate, while Sample Solution 1 before room temperature storage ("Before room temperature storage" in this graph) and Sample Solutions 1 to 3 after room temperature storage ("Containing no inhibitor", "AEBSF", and "AEBSF+PMSF" in this graph) are plotted along the abscissa. In Sample Solution 1 containing no protease inhibitor, S100P of any of the pancreatic juice specimens was almost degraded after room temperature storage. On the other hand, in Sample Solutions 2 and 3 containing the protease inhibitor, S100P was detected from any of the pancreatic juice specimens. In particular, in Sample Solution 3 containing both AEBSF and PMSF, the S100P concentration was maintained high. The above-mentioned results have revealed that mixing of at least one, two or more sulfonyl fluoride-containing sulfone-based compounds improves the stability of S100P in pancreatic juice even stored at room temperature.

Example 3

With a view to improving the storage performance of pancreatic proteins further, it was studied whether the storage stability of S100P was influenced by the combined use of the sulfonyl fluoride-containing sulfone-based compound and TLCK, that is, another sulfone-based compound. Seven human clinical specimens were used.

Described specifically, sample solutions were prepared as follows: (1) Sample Solution 1: AEBSF, obtained by adding AEBSF (final concentration: 4 mM) to the human clinical specimens. (2) Sample Solution 2: AEBSF+PMSF, obtained by adding AEBSF (final concentration: 4 mM) and PMSF (final concentration: 1 mM) to the human clinical specimens. (3) Sample Solution 3: AEBSF+PMSF+Aprotinin, obtained by adding AEBSF (final concentration: 4 mM), PMSF (final concentration: 1 mM) and Aprotinin (final concentration: 3 µM) to the human clinical specimens. (4) Sample Solution 4: AEBSF+PMSF+TPCK, obtained by adding AEBSF (final concentration: 4 mM), PMSF (final concentration: 1 mM), and TPCK (final concentration: 1 mM) to the human clinical specimens. (5) Sample Solution 5: AEBSF+PMSF+TLCK, obtained by adding AEBSF (final concentration: 4 mM), PMSF (final concentration: 1 mM), and TLCK (final concentration: 1 mM) to the human clinical specimens. The sample solutions were each prepared using a buffer attached to CircuLex S100P ELISA Kit (product of Cyclex Inc., Catalog number: CY-8060). After those sample solutions were each allowed to react by incubating them at 25° C. for 16 hours (after storage at room temperature), detection of S100P was performed in a manner similar to that of Example 2.

As a control, Sample Solutions 1 to 5 were prepared in a manner similar to that described above except freeze storage was performed instead of room temperature storage and detection of S100P from the sample solutions was performed in a manner similar to that of Example 2.

Figure 4:
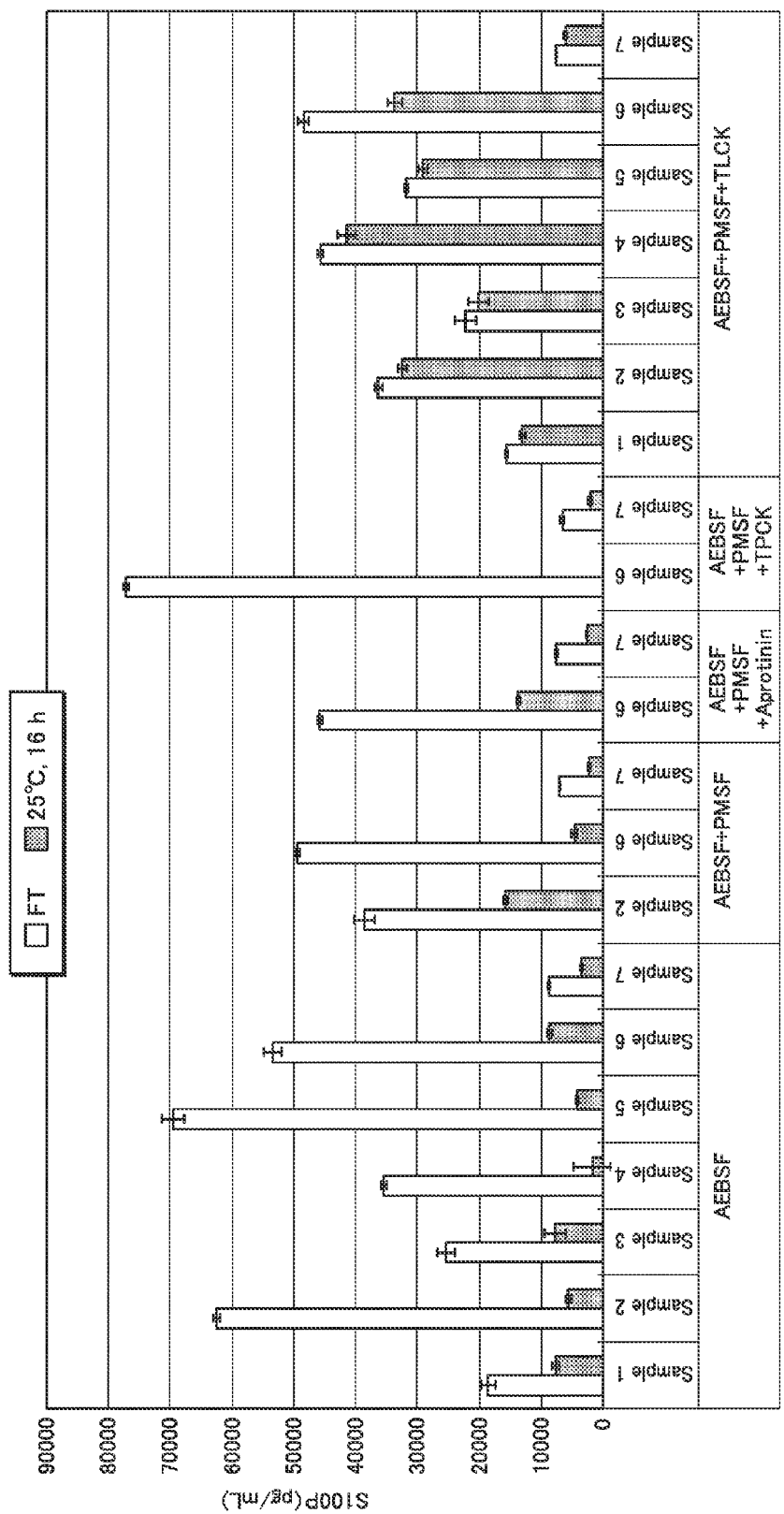
FIG. 4 shows the measurement results of the amount of S100P in the respective sample solutions in Example 3.

Measurement results are shown in FIG. 4. The concentration of S100P is plotted along the ordinate, while Sample Solutions 1 to 5 ("AEBSF", "AEBSF+PMSF", "AEBSF+PMSF+Aprotinin", "AEBSF+PMSF+TPCK", and "AEBSF+PMSF+TLCK" in the graph) of the human pancreatic juice specimens 1 to 7 are plotted along the abscissa. The term "FT" in the graph shows the results after freeze storage without room temperature storage and the term "25° C., 16 h" shows the results after incubation at 25° C. for 16 hours (after room temperature storage), respectively. As a result, in the sample solutions after frozen storage, S100P was detected, though varying in amount, from all the human pancreatic juice specimens irrespective of the kind of the protease inhibitor added. On the other hand, in Sample 1 solutions containing only AEBSF or Sample 2 solutions containing both AEBSF and PMSF, S100P was detected from all the human pancreatic juice specimens, but the detection amount was very small compared with that after freeze storage. During room temperature storage, most of S100P was degraded or modified. In Sample 5 Solutions containing AEBSF, PMSF, and TLCK, on the other hand, all the human pancreatic juice specimens showed an S100P concentration ratio remaining as high as about 70% or more of that after freeze storage. In Sample 3 Solutions containing AEBSF, PMSF, and Aprotinin or Sample 4 Solutions containing AEBSF, PMSF, and TPCK, the remaining ratio was not so high as that of Sample 5 Solutions containing AEBSF, PMSF, and TLCK. The above-mentioned results have revealed that by using at least one sulfonyl fluoride-containing protease inhibitor and an amino acid chloromethyl ketone having trypsin-like serine protease inhibitory activity such as TLCK in combination, S100P in pancreatic juice can be stored very stably even at room temperature.

Example 4

An effect of a protease inhibitor for storage stability of S100P in a pseudo artificial pancreatic juice and that for storage stability of S100P in a human clinical specimen were compared. As a S100P-containing pseudo artificial pancreatic juice, a solution obtained by adding S100P (standard preparation) to a pancreatin solution to give a concentration of 25 ng/mL was used.

More specifically, sample solutions were prepared as follows: (1) Sample Solution 1: containing no inhibitor, obtained by mixing 25 ng/mL of an S100P (standard preparation) solution with the two human clinical specimens (human pancreatic juice specimens 1 and 2) used in Example 3 and the pseudo artificial pancreatic juice. (2) Sample Solution 2: AEBSF, obtained by adding AEBSF (final concentration: 4 mM) to Sample Solution 1. (3) Sample Solution 3: AEBSF+PMSF, obtained by adding AEBSF (final concentration: 4 mM) and PMSF (final concentration: 1 mM) to Sample Solution 1. (4) Sample Solution 4: AEBSF+PMSF+TLCK, obtained by adding AEBSF (final concentration: 4 mM), PMSF (final concentration: 1 mM) and TLCK (final concentration: 1 mM) to Sample Solution 1. Each of the sample solutions was prepared using a buffer attached to CircuLex S100P ELISA Kit (product of Cyclex Inc., Catalog number: CY-8060). After the sample solutions were allowed to react by incubating them at 25° C. for 16 hours (after storage at room temperature), detection of S100P was performed in a manner similar to that of Example 2.

As a control, after Sample 1 Solutions prepared in a manner similar to that described above were subjected to freeze storage instead of room temperature storage, detection of S100P was performed in a manner similar to that of Example 2.

Figure 5:
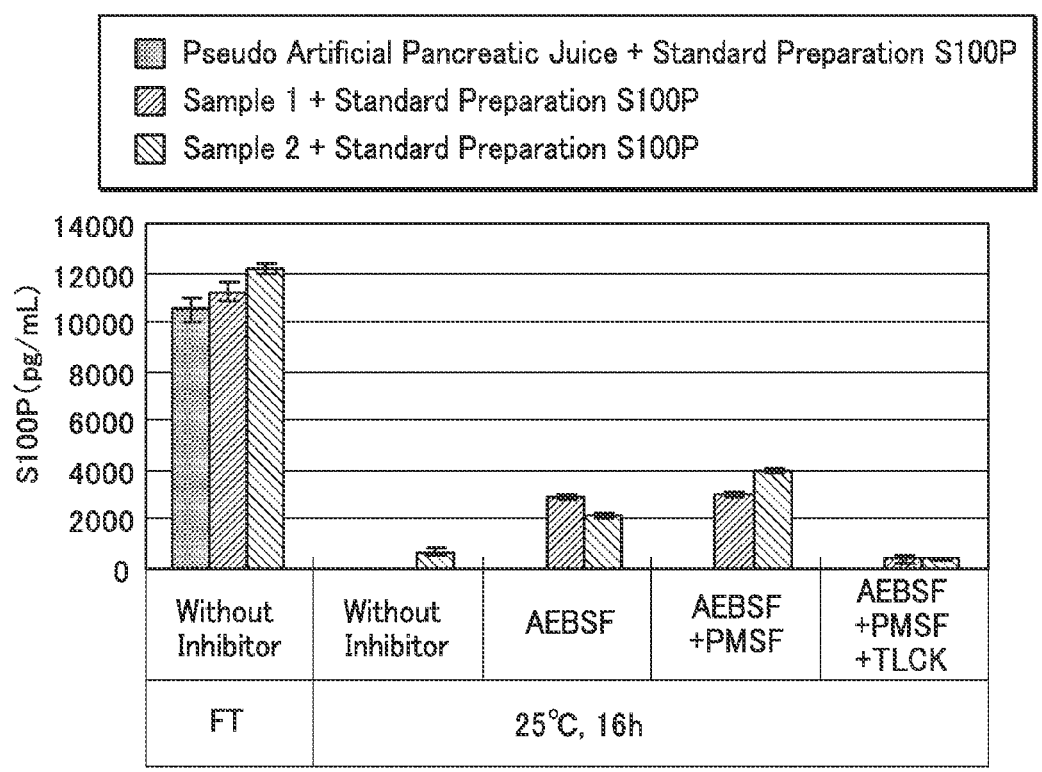
FIG. 5 shows the measurement results of the amount of S100P in the respective sample solutions in Example 4.

Measurement results are shown in FIG. 5. The concentration of S100P is plotted along the ordinate, while Sample Solutions 1 to 4 using the human pancreatic juice specimens 1 and 2 and the S100P-containing pseudo artificial pancreatic juice ("Without inhibitor", "AEBSF", "AEBSF+PMSF", and "AEBSF+PMSF+TLCK" in the graph) are plotted along the abscissa. The term "FT" in the graph shows the results after freeze storage without room temperature storage and the term "25° C., 16 h" shows the results after incubation at 25° C. for 16 hours (after room temperature storage). As a result, in the sample solutions after freeze storage, S100P was detected from both the human pancreatic juice specimen and the pancreatin solution. On the other hand, with regard to the sample solutions after room temperature storage, no S100P was detected from the pancreatin solutions irrespective of the presence or absence or the kind of the protease inhibitor. With regard to the human pancreatic juice specimens 1 and 2, the detection amount of S100P is greater in Sample Solutions 2 and 3 containing AEBSF or AEBSF and PMSF than in Sample 1 Solutions containing no protease inhibitor, suggesting that the protease inhibitor added is effective for improving the room temperature stability of S100P. On the other hand, in both the human pancreatic juice specimens, different from the results of Example 3, the amount of S100P detected was smaller in Sample Solution 4 containing AEBSF, PMSF, and TLCK than in Sample Solutions 2 or 3 containing no TLCK. These results have revealed that although the reason is not clear, a room temperature storage stability effect for S100P produced by using a sulfonyl fluoride-containing protease inhibitor such as AEBSF and a trypsin-like serine protease inhibitor, such as TLCK, belonging to a group of amino acid chloromethyl ketones in combination is valid for S100P (endogenous S100P) originally contained in a biological sample such as pancreatic juice or duodenal juice collected from a living body but not valid for S100P (exogenous S100P) added later.

INDUSTRIAL APPLICABILITY

The preservation method and storage kit disclosed herein enable stable storage of particularly S100P among proteins in biological samples such as pancreatic juice and duodenal juice at room temperature so that they can be used in the field of analyzing S100P in pancreatic juice, particularly in the field of clinical tests for diagnosis and treatment of pancreatic cancer.

The invention claimed is:

1. A method for preserving S100 calcium binding protein (S100P) in pancreatic juice or duodenal juice, comprising adding to the juice:
   phenylmethylsulfonyl fluoride (PMSF), 4-(2-aminoethyl)-benzenesulfonyl fluoride) (AEBSF), and
   N-a-tosyl-L-lysine chloromethyl ketone (TLCK)
   in an amount sufficient to preserve the S100P.

2. The method of claim 1, further comprising storing the sample at room temperature.

3. The method of claim 1, wherein
   PMSF is added to a final concentration of at least 1 mM;
   AEBSF is added to a final concentration of at least 4 mM and;
   TLCK is added to a final concentration of at least 0.1 mM.

4. The method of claim 1, wherein the S100P in the pancreatic juice or the duodenal juice consists of an endogenous S100P.

5. The method of claim 2, wherein an amount of the S100P in the pancreatic juice or the duodenal juice is at a first level after storage at freezer temperature for sixteen hours and at a second level after storage at room temperature for sixteen hours, and wherein the second level is at least 70% of the first level.

6. A method for detecting S100P, comprising:
   preparing a sample containing pancreatic juice by adding phenylmethylsulfonyl fluoride (PMSF), 4-(2-aminoethyl)-benzenesulfonyl fluoride) (AEBSF), and N-a-tosyl-L-lysine chloromethyl ketone (TLCK) to a biological sample containing pancreatic juice; and
   detecting S100P in the sample containing pancreatic juice.

7. The method of claim 6, wherein the S100P in the pancreatic juice or the duodenal juice consists of an endogenous S100P.

8. The method of claim 6, wherein an amount of the S100P in the pancreatic juice or the duodenal juice is at a detection first level after storage at freezer temperature for sixteen hours and at a second detection level after storage at room temperature for sixteen hours, and wherein the second level is at least 70% of the first level.

* * * * *